(12) United States Patent
Gylleby (10) Patent No.: US 11,430,550 B2
(45) Date of Patent: Aug. 30, 2022

(54) DEVICE FOR PROVIDING PERCEIVED HEALTH STATUS

(71) Applicant: SHL Medical AG, Zug (CH)

(72) Inventor: Stefan Gylleby, Drottningholm (SE)

(73) Assignee: SHL MEDICAL AG, Zug (CH)

( * ) Notice: Subject to any disclaimer, the term of this patent is extended or adjusted under 35 U.S.C. 154(b) by 472 days.

(21) Appl. No.: 16/467,886

(22) PCT Filed: Nov. 28, 2017

(86) PCT No.: PCT/EP2017/080690
§ 371 (c)(1),
(2) Date: Jun. 7, 2019

(87) PCT Pub. No.: WO2018/104113
PCT Pub. Date: Jun. 14, 2018

(65) Prior Publication Data
US 2020/0090797 A1    Mar. 19, 2020

(30) Foreign Application Priority Data
Dec. 9, 2016  (SE) .................................. 1651628-8

(51) Int. Cl.
*G16H 10/65*  (2018.01)
*A61B 50/36*  (2016.01)
(Continued)

(52) U.S. Cl.
CPC ........... *G16H 10/65* (2018.01); *A61B 50/362* (2016.02); *A61B 90/96* (2016.02); *A61B 90/98* (2016.02)

(58) Field of Classification Search
CPC ...... G16H 10/65; G16H 20/10; A61B 50/362; A61B 90/96; A61B 90/98; A61B 90/90; A61B 50/36
See application file for complete search history.

(56) References Cited

U.S. PATENT DOCUMENTS 6,273,817 B1    8/2001  Sultan
6,529,446 B1 *  3/2003  de la Huerga ........ A61J 7/0481
                                                      368/10
(Continued)

FOREIGN PATENT DOCUMENTS

CN       204484328 U    7/2015
EP         3103793 A1  12/2016
(Continued)

OTHER PUBLICATIONS

Medicare Program: Hospital Outpatient Prospective Payment and Ambulatory Surgical Center Payment Systems and Quality Reporting Programs; Organ Procurement Organization Reporting and Communication; Transplant Outcome Measures and Documentation Requirements; etc US Official News Nov. 14, 2016: NA. (Year: 2016).*

(Continued)

*Primary Examiner* — Linh Giang Le
(74) *Attorney, Agent, or Firm* — McDonnell Boehnen Hulbert & Berghoff LLP (57) ABSTRACT

The present invention relates to an information provider for providing information on perceived health status of a patient, comprising a body, a data carrier containing data regarding at least one health status attached to said body. The invention is characterised in that said data carrier is designed to provide said data regarding at least one health status to a reader configured to read said data carrier.

20 Claims, 6 Drawing Sheets

(51) Int. Cl.
*A61B 90/96* (2016.01)
*A61B 90/98* (2016.01)

(56) References Cited

U.S. PATENT DOCUMENTS

| | | |
|---|---|---|
| 2003/0083556 A1 | 5/2003 | Cosentino et al. |
| 2005/0065640 A1 | 3/2005 | Mallett et al. |
| 2007/0299687 A1 | 12/2007 | Palmer et al. |
| 2008/0139866 A1 | 6/2008 | Fisher et al. |
| 2009/0037204 A1* | 2/2009 | Tan .................. G06Q 30/06 705/325 |
| 2009/0043253 A1 | 2/2009 | Podiama |
| 2009/0149719 A1 | 6/2009 | Wariar et al. |
| 2011/0046971 A1 | 2/2011 | Young et al. |
| 2011/0178820 A1 | 7/2011 | Soni et al. |
| 2013/0237949 A1 | 9/2013 | Miller |
| 2014/0374294 A1 | 12/2014 | Joyce |
| 2016/0039591 A1* | 2/2016 | Kinzer ................ A61K 31/616 424/10.3 |

FOREIGN PATENT DOCUMENTS

| | | | |
|---|---|---|---|
| GB | 2462449 A | 2/2010 | |
| WO | 02081015 A1 | 10/2002 | |
| WO | WO-02081015 A1 * | 10/2002 | ........... A61J 7/0481 |
| WO | 2014204958 A1 | 12/2014 | |
| WO | 2016055351 A1 | 4/2016 | |

OTHER PUBLICATIONS

Geng Yang; Li Xie; Matti Mäntysalo; Xiaolin Zhou; Zhibo Pang; Li Da Xu; Sharon Kao-Walter; Qiang Chen; Li-Rong Zheng. "A Health-IoT Platform Based on the Integration of Intelligent Packaging, Unobtrusive Bio-Sensor, and Intelligent Medicine Box." IEEE Transactions on Industrial Informatics. (Year: 2014).*

Office Action issued in Swedish Patent Application No. 1651628-8 dated Jun. 26, 2017.

Search Report issued in Taiwanese Patent Application No. 106142353 dated Sep. 3, 2018.

English Translation of Abstract of Chinese Patent No. 204484328 dated Jun. 7, 2019.

* cited by examiner

DEVICE FOR PROVIDING PERCEIVED HEALTH STATUS

CROSS REFERENCE TO RELATED APPLICATIONS

The present application is a U.S. National Phase Application pursuant to 35 U.S.C. § 371 of International Application No. PCT/EP2017/080690 filed Nov. 28, 2017, which claims priority to Swedish Patent Application No. 1651628-8 filed Dec. 9, 2016. The entire disclosure contents of these applications are hereby incorporated by reference into the present application.

TECHNICAL AREA

The present invention pertains to a device capable of providing information regarding perceived health status and in particular a device that can communicate the health status perceived by a patient to a unit that can handle the information.

BACKGROUND OF INVENTION

With the ever increasing demands on more cost-effective healthcare, self-medication and home treatment has increased over the last decades. With the development of internet of things and connected devices, the healthcare is exploring the possibilities of monitoring the use of medical delivery devices at home and thus the adherence of patients. In this regard a number of systems are being developed that can measure and monitor not only when and how a patient is using devices for self-treatment but also hard data as regards measured values.

Hard data might be important in some cases to see the progress of the treatment of the patient in order to evaluate if the treatment scheme set up is working properly. However, this often requires additional equipment apart from the medical delivery devices that need to be operated by the patient or a helper to the patient. On the one hand, the home treatment is now becoming complex since many devices need to be operated, which may be difficult to many users and on the other hand these devices produce vast amounts of data, data that has to be handled and processed in order to obtain results that are understandable and useful to e.g. patient and/or a doctor of a patient.

On the other hand for many cases and treatment schemes hard data might not be needed for monitoring the progress of a patient following a treatment scheme, it might suffice to obtain the perceived health status in order to monitor the progress, which is done in a much easier and straightforward way. However, even the perceived health status of the patient has to be handled in some way in order to be presented to the patient and his/her doctor.

There is thus room for improvements in this technical field.

BRIEF DESCRIPTION OF INVENTION

The present invention aims to remedy the drawbacks of the state of the art solutions regarding obtaining health status from patients. This aim is solved by the features of the independent claim. Preferable embodiments form the subject of the dependent patent claims.

According to the invention, it pertains to an information provider for providing information on perceived health status of a patient. The information provider comprises a body and a data carrier containing data regarding at least one health status attached to said body.

The data carrier is designed to provide the data regarding at least one health status to a reader configured to read the data carrier. In this manner, the patient can use the information provider to give feedback and information regarding the perceived health status, i.e. how the patient is feeling at the moment. This may be used in connection with the administration of a medicament, such as swallowing a tablet or injecting a dose of medicament. In this regard, the patient may be ordered to wait a certain time period after the administration. As an alternative, the patient may use the information provider in the morning to provide information regarding the perceived health status after a night's sleep. In any event, the information providers are used on a regular basis during e.g. the duration of a treatment scheme.

According to one feasible solution, the data carrier may contain data regarding one specific health status. In this case, one specific information provider is used for a specific perceived health status. In this regard, different information providers may comprise different health statuses that may be provided to a patient, enabling the patient to choose an information provider containing a health status that best corresponds to the patient's perceived health status. Thus, the patient is provided with a set of information providers, which could cover a range from e.g. happy to depressed, with a number of intermediate statuses.

As an alternative, the information provider may be configured and designed such that the data carrier comprises a plurality of different health statuses. In this case, the information provider may further comprise manually operable activation elements, enabling choosing a specific health status from a plurality of health statuses. With such a solution, the number of information providers given to the patient can be reduced. The patient then has to perform some action in order to choose the health status that best fits the perceived health status. The design of the information provider may then be such that the activation elements may comprise removable layers of material, wherein removal of material exposes or manipulates the data carrier to provide data regarding a chosen health status. The removal of layers of material may comprise paper layers that are torn off, opaque material that is scraped off, adhesive stickers that are peeled off, etc. The main aspect is however that only the part of the data carrier containing the chosen health status is exposed.

According to a further aspect of the invention, the data carrier may comprise additional information pertaining to actual conditions of the patient. Thus, in addition to perceived health status, additional information regarding measured data or experienced occurrences could be provided from the information providers. As examples, the additional data pertaining to actual conditions could be any of body temperature, hours of sleep, blood pressure. According to a preferable solution in that regard, the additional data pertaining to actual conditions may presented as sub-ranges within a total range.

As with the information providers having a plurality of perceived health statues, in the case of plurality of additional data pertaining to actual conditions, manually operable activation elements may be arranged, enabling choosing a specific actual condition from the plurality of health statuses.

Regarding the reader configured to read the data carrier, it may preferably be operably connected to a medical waste container and in this case data may be read by the reader when the information provider is in the vicinity of the reader.

This is an advantage when the patient has medicament delivery devices that are to be discarded after use. The trends are that these medicament delivery devices should also be registered by appropriate readers when they are discarded and in that case, the reader could also be used for obtaining information from the information providers. Functionality that is already available to the patient may then be used for additional purposes. Since the medicament delivery devices are discarded into the medical waste containers and are read there by the readers, the information providers could also be designed and intended to be entered into the medical waste container in order to be read by the reader. Further, in order to be easy to handle and not to take up too much space, regardless of whether the information providers are discardable or re-usable, the body may be made of material of sheet form, the sheet material comprising thin sheets of plastic, metal, wood, cardboard, paper or laminated combinations thereof. As a further alternative, the information provider may be comprised in a primary package for a medicament. This is an efficient solution because the patient is provided with information providers already "included" when a medicament delivery device that is in a treatment scheme is delivered to the patient. No additional components may be provided.

According to one feasible solution, the data carrier may comprise optically readable elements. These readable elements may comprise bar codes, QR-codes, OCR-readable characters, micro-dot patterns etc. They could also comprise colour fields where one distinct colour corresponds to a specific health status. As an alternative, the data carrier may comprise near frequency communication elements such as RFID or NFC elements. Regarding the reader, it may be comprised in a base on which said medical waste container may be placed.

These and other aspects of, and advantages with, the present invention will become apparent from the following detailed description of the invention and from the accompanying drawings.

BRIEF DESCRIPTION OF DRAWINGS

In the following detailed description of the invention, reference will be made to the accompanying drawings, of which FIG. 1 discloses a safety container and an information obtaining unit.

DETAILED DESCRIPTION OF THE INVENTION

In the following description, the wording smart devices will be used. In this context, smart devices may include electronic devices that are provided with processors that are capable of running computer programs and storage space to store programs as well as data retrieved from different external sources. It is further to be understood that the smart devices are provided with communication systems that are capable of communicating with data networks in order to access different databases. It is to be understood that databases may be accessed via the internet, so called cloud services, and/or databases that are connected directly to and accessed via local area networks. It is further to be understood that the smart devices in this context comprise some sort of human-machine interface for two-way communication. The human-machine interface may comprise displays, keyboards, microphones, loudspeakers, I/O-ports for connection of peripherals. Further the smart devices may be provided with antennas for wireless communication with the networks. Also, the smart devices may be arranged with receiving and transmitting mechanisms capable of communicating with RFID/NFC tags as well as programs capable of establishing and handling the communication with the RFID/NFC tags.

Further, in the following description, the wording medicament delivery device will be used. In this context, medicament delivery devices may include a number of devices capable of delivering certain doses of medicament to a user, such as e.g. injection devices with or without injection needles, inhalers of all kinds, such as powder, aerosol driven, gas, nebulizers having mouth or nasal pieces, but in particular medicament delivery devices that may cause injuries or be harmful if not handled properly, especially after use.

The present invention relates to a device for providing information regarding the perceived health status of a patient, possibly together with additional information in connection to the health status. The device will in the following description be named information provider.

Different types of statuses may e.g. be happy or content, i.e. feeling well, unhappy or discontent, i.e. feeling bad or sick, or statuses in between. Additional information may be number of hours the patient has slept during a certain time span, like a night or during 24 hours; if the patient has experienced nausea, headache, dizziness, increased pulse, dry mouth etc.

In order to collect this information in an uncomplicated and intuitive way for the patient, the present invention utilizes information providers that are pre-prepared with information regarding the perceived health status of patients. Depending on application as will be described below, the devices may have different physical shapes and configurations.

Figure 3A:
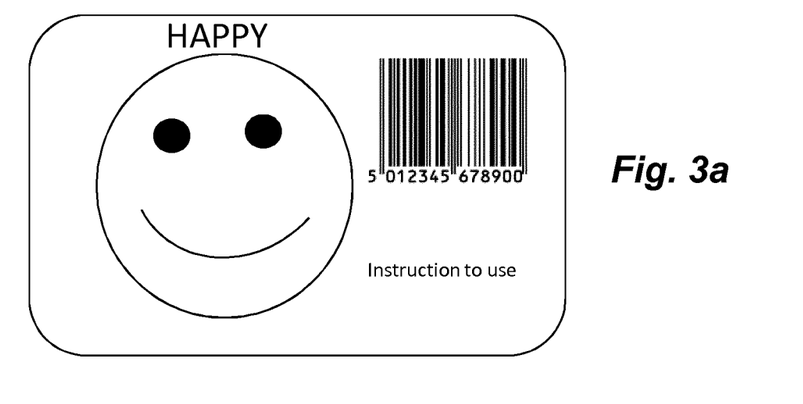

In a first basic form, each information provider is provided with a data carrier containing one specific type of information regarding the perceived health status, like for example happy/well/no symptoms, ok/intermediate/some symptoms, sad/unwell/heavy symptoms. Further, each information provider is provided with indicia on an outer surface indicating to a patient or user the type of pre-prepared information that the information provider contains. The indicia may be readable information like "I feel happy", FIG. 3a, but may instead or in addition, comprise symbols or pictures like a smiling face or a hand having the thumb up. The information provider may contain further handling instructions, FIG. 3a, as to how the information provider is to be used or held in relation to cooperating information receivers or readers that are to obtain the information from the information provider. These handling instructions may also be in written form and/or symbol form.

Figure 3B:
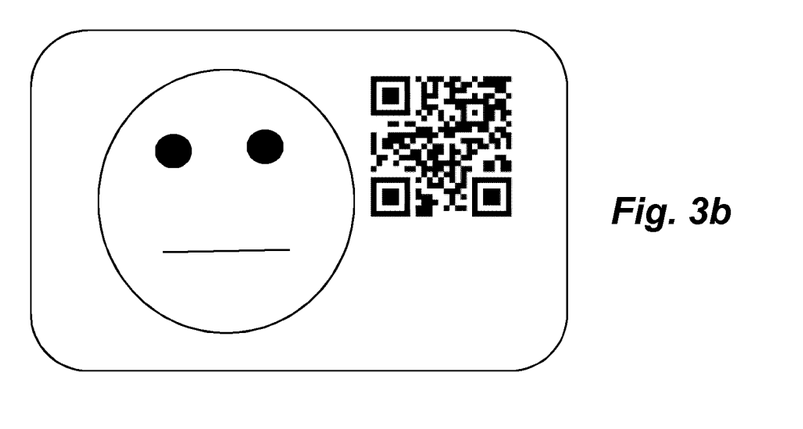

The information of the data carrier may be provided in several different ways, but will preferably be connected to the intended receiver or reader as will be described. In one basic solution the information is provided as a data carrier in printed or visual form on a surface of the device. This may include any of bar code, FIG. 3a, QR-code, FIG. 3b, alpha-numeric code, micro-dot patterns and the like that may be read by an optical reader of a receiver.

Figure 3C:
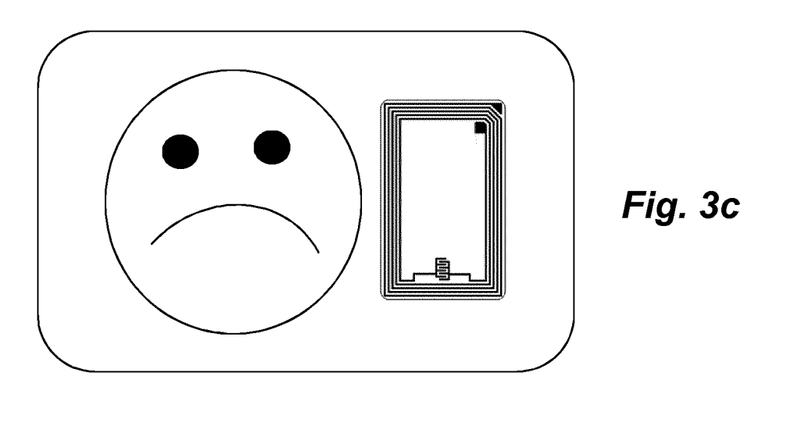

Another solution is to utilize near frequency communication technologies like RFID or NFC, FIG. 3c. In that regard an appropriate RFID or NFC tag is embedded as a data carrier in the information provider, comprising an antenna that is capable of transmitting the pre-prepared information comprised in the tag to a receiver. Appropriate activation circuits may further be arranged as will be described.

In one physical form the information provider may be made of a material in sheet form, forming some sort of card or note of appropriate size. The material could be cardboard, thick paper, plastic, wood, metal. Further the information provider may be laminated in order to embed elements wherein different materials could be used in the laminated information provider in order to obtain the desired functionality. If the above mentioned RFID or NFC technologies are used, then the tags may be embedded between layers of the laminated information provider. As will be apparent from the following description, these types of information providers may either be discardable, i.e. they are used only once for providing information regarding the health status of the patient or they may be re-usable, i.e. used several times for providing the health status information.

Figure 4:
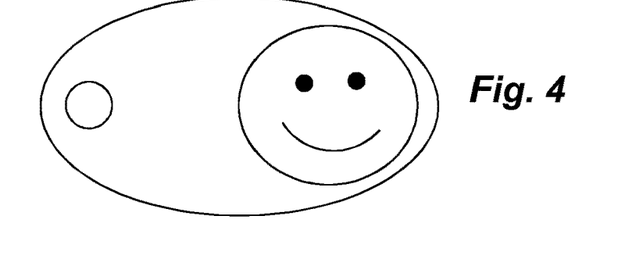

In addition to the sheet form, the information provider may further have other shapes or sizes. For example the information provider may have the form of a button or tag, FIG. 4, often made of plastic. These types of information provider are typically intended to be re-used. A patient or user is then provided with a set of these tags, each having different specific information. Of course other shapes may be employed as desired. If near frequency technologies are used, the tags may be built into or even molded into the information provider, protecting the tags.

Figure 5:
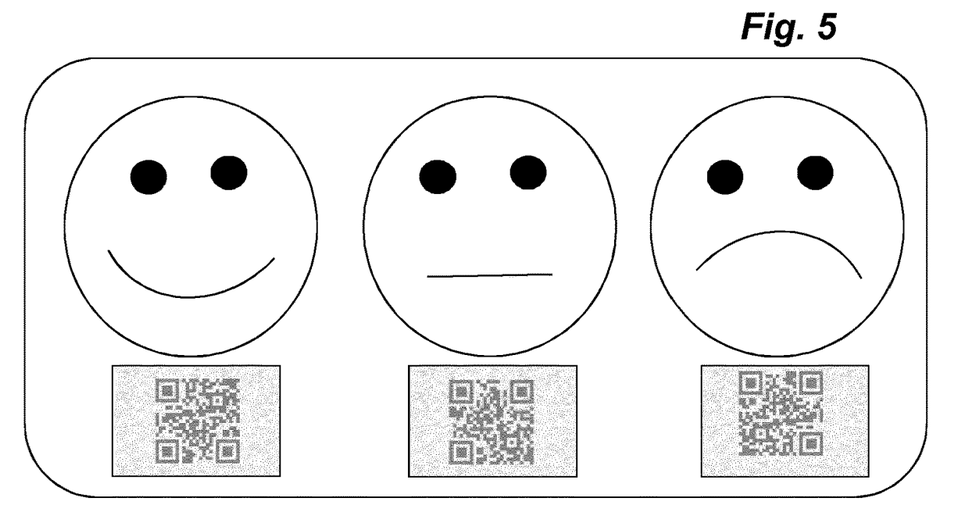

In a further form the information provider may contain more than one specific type information, i.e. the data carrier contains a plurality of different information regarding the health status of the patient. Here the patient has to perform some sort of action in order for the information provider to provide the intended information. In one embodiment, the information provider contains for example information regarding all health statuses happy/well/no symptoms, ok/intermediate/some symptoms, sad/unwell/heavy symptoms and depending on how the patient feels, the information provider is manipulated to display that particular health status. If printed or optically readable information is used, the areas containing different information may be initially covered by material so that they are hidden, FIG. 5. The material may for example be paper or cardboard layers that can be torn off in order to expose the intended and desired information. The material may also be opaque coating that is scraped off by e.g. a coin in order to expose the information.

Figure 6:
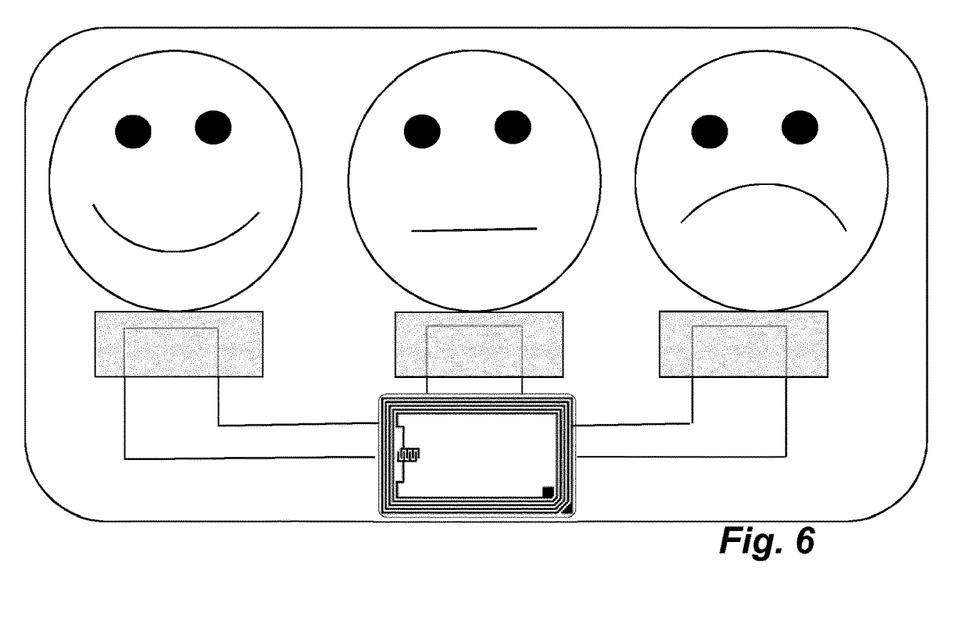

If near frequency technologies are employed that contains a plurality of information, the data carrier of the information provider may be arranged with different areas having different circuits defining different specific health statuses and when an area is manipulated by a patient or user, the circuit is affected and information pertained to that specific health status may be transmitted to a receiver, FIG. 6. The affected circuit may be manipulated by scraping off a layer such that a circuit is broken. In this regard, it may be feasible to use printed electronics technologies.

As mentioned above the information provider may comprise additional information that is connected or pertinent to the main information regarding the perceived health status. For instance the additional information may comprise more specific health details like the number of hours sleep, fever temperature, blood pressure, resting pulse, etc. This information may be presented as ranges that can be chosen and exposed by the patient as mentioned above by tearing off or scraping.

Figure 7:
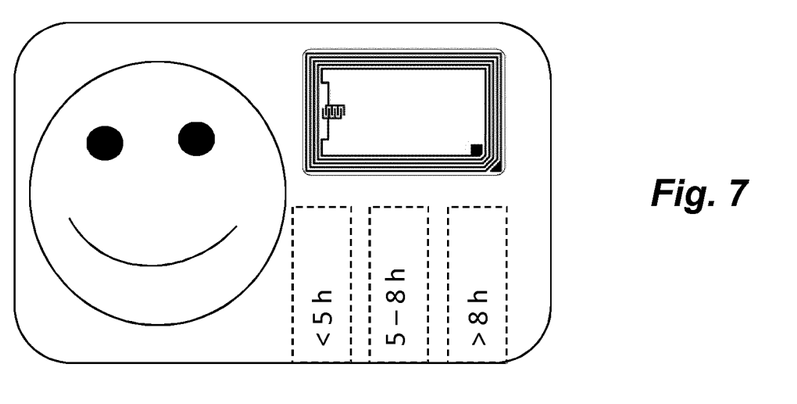
Figure 8:
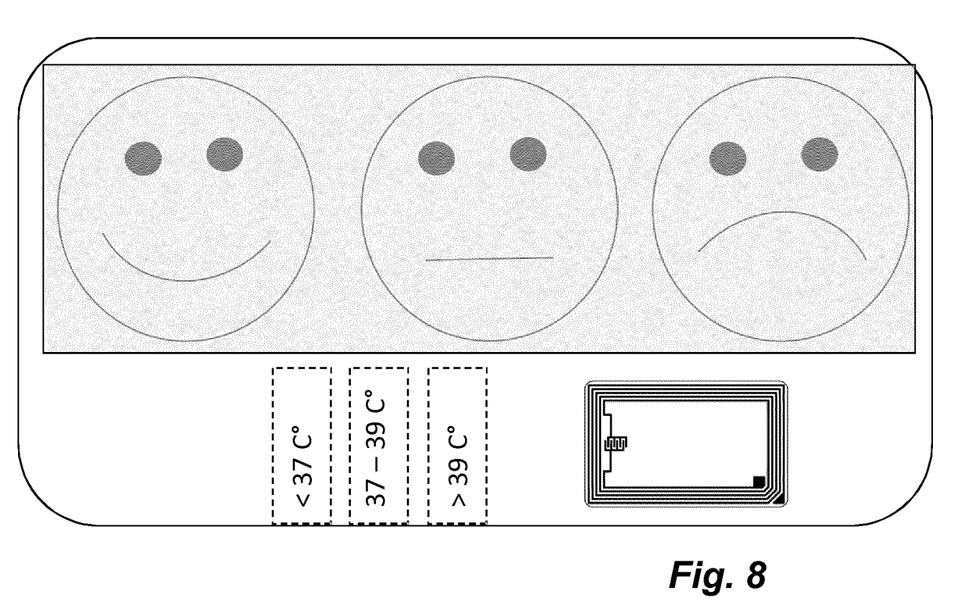

The additional information may be arranged in the data carrier on an information provider having one specific "basic" perceived health status. As an example, the card may contain "happy/content" information and the patient may then expose "slept 7-9 hours", FIG. 7. The additional information may also be arranged on a device having a plurality of "basic" perceived health statuses. As an example, the patient may first manipulate the device to display information regarding "main" health status, such as "bad/unwell" and then chose a fever range such as "38-39" degrees, FIG. 8.

Figure 9A:
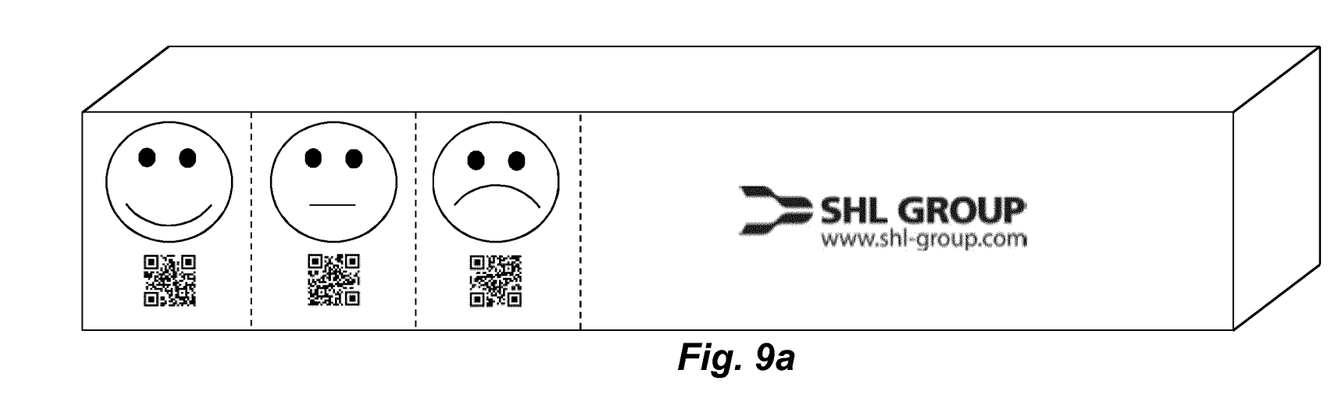

Regarding the supplying of patients and users with information providers this may be done from several sources. One logical source is from the healthcare provider and perhaps the doctor or clinic that has responsibility for the patient and that has set up a treatment scheme. Also, or instead, the information providers may be supplied in connection with the medicament to be taken by the patient and in that regard the information providers are supplied by the pharma company that produces and markets the drug. If the information providers are supplied in connection with the medicament, it is feasible that the information providers are a part of the primary package that the medicament is delivered with. As an example a primary package for a medicament delivery device is shown in FIG. 9a. Here different specific information are provided on parts of the primary package that may be torn or cut away to form separate card that can be used as described above. In this regard, many of the combinations and technologies described above may be applied on the parts of the primary package that form the information providers.

Figure 9B:
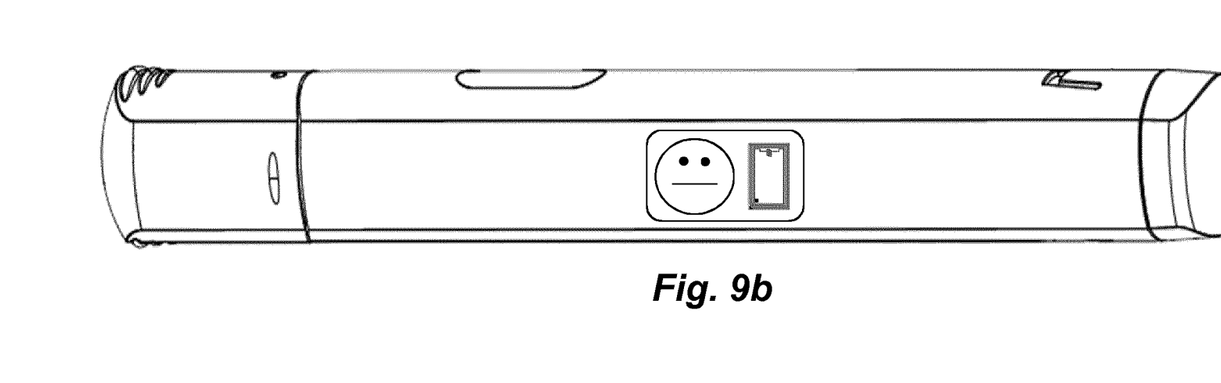

Further, instead of the information provider being a card that is discarded separately into a safety container, it may have an adhesive surface wherein the user sticks the appropriate information provider onto the medicament delivery device to be discarded, as seen in FIG. 9b.

The information provider according to the invention is intended to cooperate with suitable receivers that are capable of obtaining and handling the information obtained from the devices. Such a receiver may advantageously be operably connected to a safety container for medical waste. Operably connected is in this context regarded as being a standalone unit that may be releasibly connected to a safety container, as a plate or stand, as a box having fastening elements to connect it to the inner or outer surface of a safety container or a lid thereof. Operably connected may also be regarded as being integrated into the waste container as an integral part, either fixedly or removably.

There are systems developed where receivers like near frequency communication readers, e.g. RFID-readers, are arranged to a safety container for obtaining information when a medicament delivery device has been discarded in the safety container, whereby the medicament delivery device is arranged with an RFID-tag. According to general instructions for the use of medicament delivery devices, each time a medicament delivery device has been used, it is to be thrown in the safety container. With such a system this is registered by the RFID-reader arranged such that it can read RFID-tags inside the safety container or in the vicinity of the safety container.

As an alternative, the receiver operably connected to the safety container may instead be an optical reader capable of reading different optical codes such as bar codes, QR codes, alpha-numeric code, micro-dot patterns and the like, whereby the medicament delivery device is arranged with such codes. Again, when a medicament delivery device is to be thrown into the safety container, its optical code is read and the discarding is registered.

Because a receiver or reader is already in use in connection with a safety container and because the medicament delivery devices used by a patient for treating a condition, often according to a treatment scheme, are thrown into the safety containers, it would be an advantage to then utilize the receiver or reader to also obtain information from the information providers containing information regarding perceived health, in particular since some of these receivers or readers are operably connected to communication mechanisms for transmitting data and information to external devices and data storage locations as will be described below.

Figure 1:
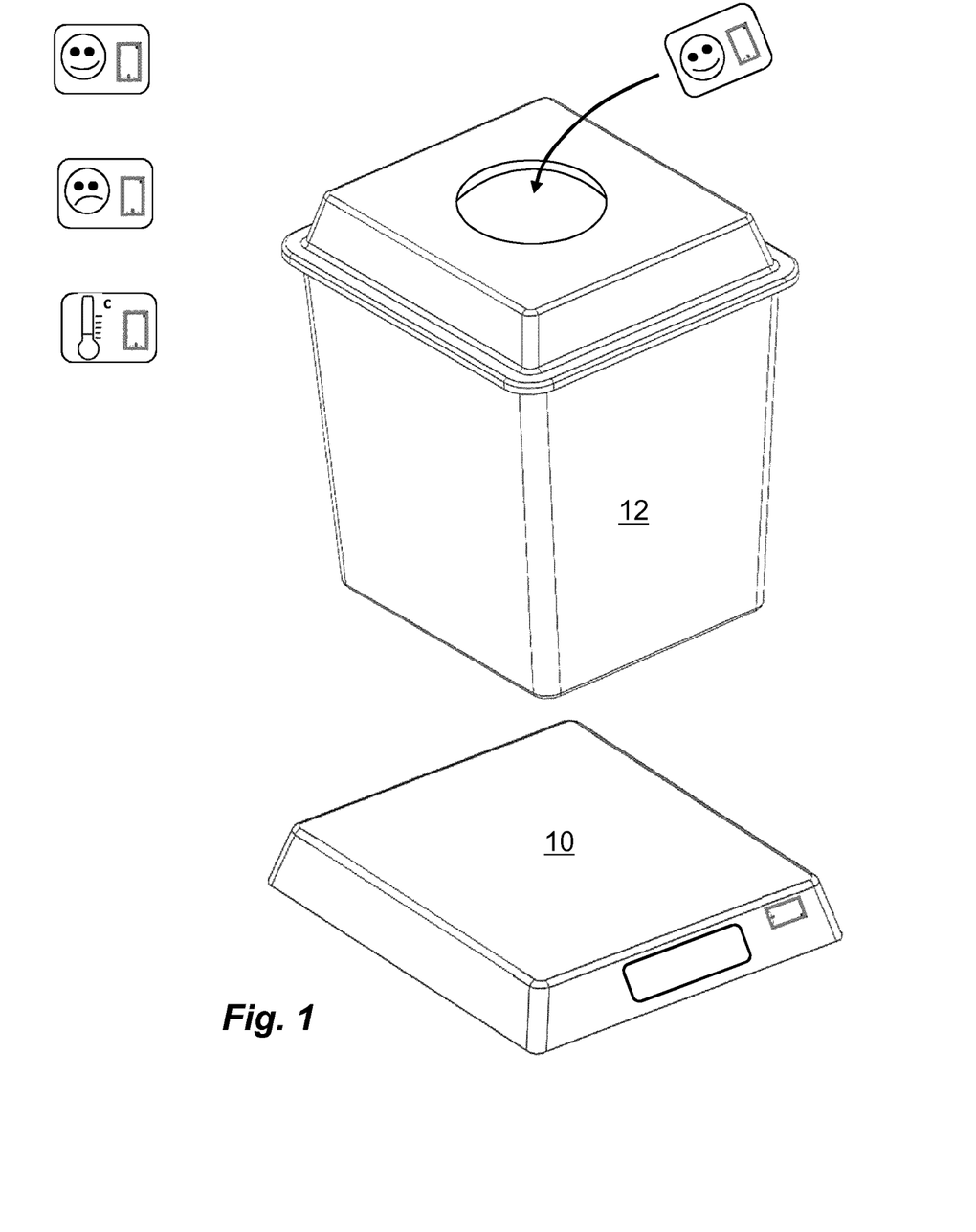

In the following a possible solution for a receiver or reader operably connected to a safety container will be described. The embodiment shown in FIGS. 1 and 2 comprises an information obtaining unit in the form of a base 10 or stand on which a safety container such as a sharps bin 12 may be placed on or attached to. The safety container 12 may be any ordinary sharps bin or medical safety box and does not require any specific features or designs. The base 10 may be arranged with a number of features and functions as will be described.

Figure 2:
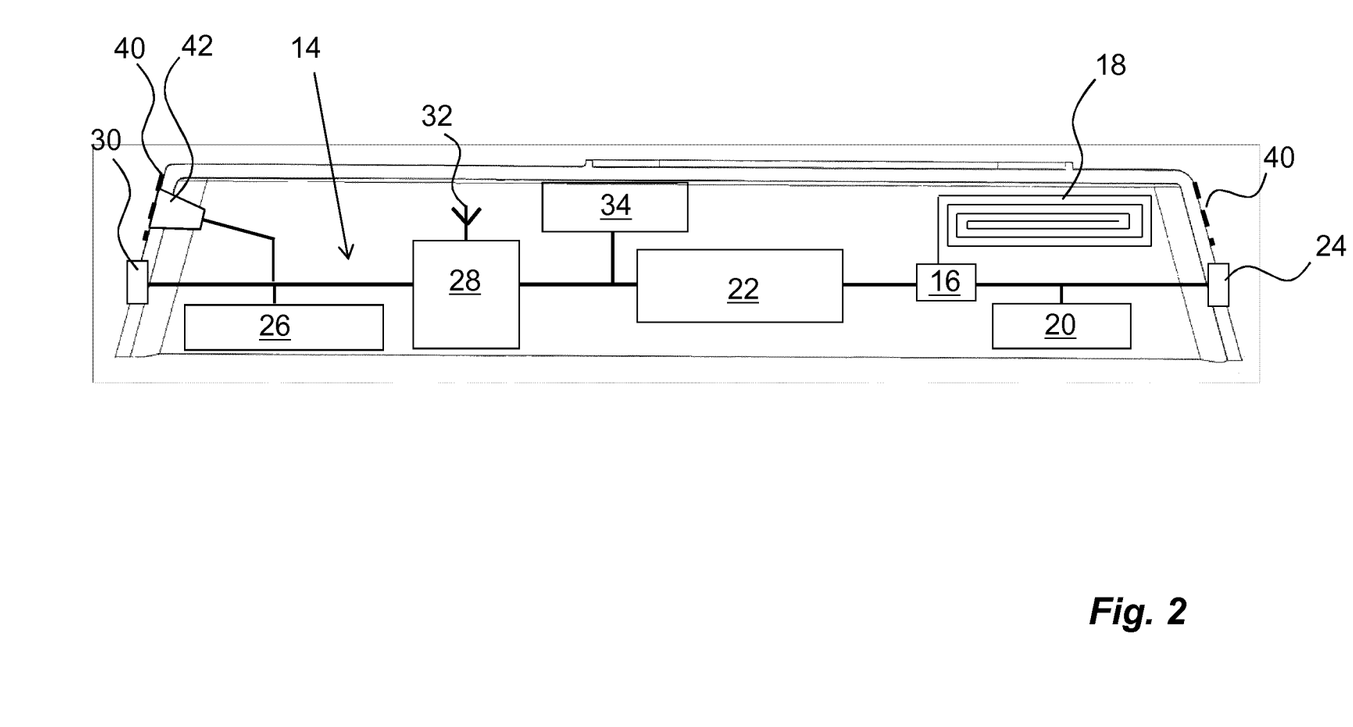
FIG. 2 shows an electronics circuit in the information unit of FIG. 1, FIGS. 3-8 show different types of information providers according to the invention, and FIG. 9 show a primary package and a medicament delivery device provided with information providers.

An electronics circuit 14 is arranged in the base, FIG. 2. It comprises an RFID reader circuit 16, which in turn comprises an antenna 18 capable of reading the RFID-tags on medicament delivery devices thrown into the safety container 12. It further comprises memory storage elements 20 for storing data retrieved by the RFID reader. Further, a processor 22 is arranged for performing a number of functions based on data program code stored in the memory storage elements. The base could also be arranged with suitable human interface devices 24 such as displays, indication lamps, keyboards, touch screens, loudspeakers, microphones etc. depending on the desired functions. The electronic circuit is further arranged with a suitable power source 26 for its function, which could be batteries, photovoltaic panels, or power from mains.

The base is further arranged with a communication circuit 28. This may comprise suitable connection elements 30 such as sockets for USB-devices and/or cables, Ethernet-sockets, and the like attachment elements for cables suitable for communication. Also, the communication circuit may be provided with transmitting elements 32 for wireless communication. The wireless communication elements may comprise near range communication technology such as RFID, NFC or the like, as well as Bluetooth, Ant, Zigbee, just to mention a few.

However, the wireless communication elements may preferably comprise cellular radio communication networks, e.g. GSM, 3G, 4G, etc. and/or wireless local area networks, which networks can provide access for the base to the internet and thus to a large number of external data storage sources, data handling centres, etc.

One of the functions or features of the base could be that the electronics circuit may have a timer function capable of providing a time stamp of when a medicament delivery device has entered the safety container and been identified by the RFID-reader. The time stamp may then be stored in the memory of the electronics circuit. One or several stored time stamps may then be retrieved by appropriate data retrieving technologies. One such could be a portable memory connected to the I/O interface of the base. The portable memory may comprise a USB memory which may be attached to appropriate receptacles for retrieving the stored time stamps.

The USB memory may thereafter be connected to a computer or other smart device that can process the data of the time stamps. In that manner, the patient's usage behaviour over time may be monitored. The usage behaviour may be compared to a prescribed treatment scheme that the patient has received from his/her physician or other medically skilled person, whereby the adherence of the patient will be derived. Any deficiencies in the adherence can then be addressed by the physician of the patient.

Also or instead, a communication cable such as a USB cable may be connected, which cable may be attached to a computer or a smart device with its other end, whereby stored time stamps are transmitted via the cable and handled in the same manner as above. Also, or instead, the retrieved data, either by a portable memory or by cable, may be transmitted by the computer or smart device to remote information storage sources, e.g. on the internet, by using the communication capabilities of the computer or smart device.

Thereby, the user or patient may use his/her own computer or smart device for retrieving saved time stamps and to use appropriate available communication networks for transmitting the retrieved data to a dedicated information source, from which a physician or medically skilled person may obtain and process the data. The physician or skilled person may then use the communication networks transmit information to the computer or smart device of the user regarding the adherence of the patient and to alert or instruct the patient depending on the results.

However, if the communication elements are arranged in the base as such, then the base may communicate directly with external data storage sources, data handling centres etc. via the communication networks. Time stamps may then either be stored locally and transmitted at specific intervals or may be transmitted directly without storage.

Thus, as seen from the example above, the receiver or reader may be used with the device according to the invention. In its basic form when cards are used that that are provided with RFID tags and are disposable, they may be discarded into the safety container whereby the information from the cards are read and handled by the reader 18 of the electronics circuit 14. In this regard, the stored information may be handled in the same manner as the information from the discarded medicament delivery devices.

Further, instead of an RFID reader, an optical reader may be used in the same manner as above, wherein optically readable information is provided on the medicament delivery devices that are discarded, which optical reader also is used for reading the cards that are discarded in the safety container.

Instead, if re-usable devices are used, the base may be provided with an area 40 where the reader may read the information from a device that is outside the safety container. Thus, when a patient or a user is to register the perceived health, he/she merely holds a device with the chosen health status against or in the vicinity of the reading area such that the reader can obtain the information. This can apply to both optically readable information and electrically readable information. In this regard, the information obtained from a medicament delivery device to be discarded may either be obtained when the medicament delivery device has been put into the safety container as described above or may be obtained by holding the medicament delivery device against or in the vicinity of the reading area before discarding it into the safety container.

As a further alternative, it is of course possible to have several readers in the stand or in the safety container. For instance, as an example, the stand may be arranged with an RFID-reader 18 as described above for obtaining information from medicament delivery devices that have been discarded into the safety container. In addition, the stand may be provided with an optical reader 42, FIG. 2, capable of reading information regarding perceived health from the devices. In this regard, it is of course feasible to have an optical reader for the discarded medicament delivery devices and to have a near frequency reader for the devices. In any event, additional readers will increase the possibilities of reading different types of information carriers.

Regarding medicament delivered to a patient, examples above have been described in connection with medicament delivery devices such as injectors. However, it is easily understood that the use of information indicators may be used also for medicament that is delivered in other forms, such as tablets or liquid. Information providers are then supplied together with e.g. the tablets. In many instances the patients use several types of medicament and medicament in different form and many patients have therefore safety containers that can be operably connected to the above mentioned receivers/readers. It would thereby be an easy task to include the information providers from other forms of medicament and use them in the same manner as described above.

In the text and the claims, data storage may comprise a circuit capable of storing data information pertaining to certain health statuses, but it is also to be understood that data storage also comprises a switch that is closed or opened e.g. when operated, where the status of the switch indicates, and/or provides information regarding, the perceived health status.

The invention claimed is:

1. An information provider for providing information on perceived health status of a patient, comprising
   a body having an outer surface, where the body contains handling instructions that informs a user of the information provider how to use the information provider to communicate a specific health status of the user,
   a data carrier, where at least a portion of the data carrier is located on the outer surface, where the data carrier contains pre-prepared data comprising a number of possible health statuses of a user of the information provider,
   wherein the user must perform a physical manipulation of the data carrier in order that the pre-prepared data becomes accessible to the user such that the user can then select from the pre-prepared data the specific health status that is indicative of the health status of the user at the time the selection is made by the user, and
   wherein after manipulation of the data carrier and after the selection of the specific health status, the data carrier will then provide the specific health status to a reader configured to read the data carrier.

2. An information provider according to claim 1, wherein said data carrier contains pre-prepared data regarding one specific health status.

3. An information provider according to claim 2, wherein different information providers comprise different health statuses that may be provided to the user.

4. An information provider according to claim 3, wherein different information providers enable the patient to choose an information provider containing a health status that best corresponds to the patient's perceived health status.

5. An information provider according to claim 1, wherein the device further comprises manually operable activation elements, enabling choosing the specific health status from said possible of health statuses.

6. An information provider according to claim 5, wherein said activation elements comprise removable layers of material.

7. An information provider according to claim 6, wherein removal of material exposes said data carrier to provide the user access to the pre-prepared data.

8. An information provider according to claim 2, wherein said data carrier comprises additional information pertaining to actual conditions of the patient.

9. An information provider according to claim 8, wherein the device further comprises manually operable activation elements that allows the user to choose a specific actual condition from the possible health statuses.

10. An information provider according to claim 1, wherein said reader is operably connected to a medical waste container.

11. An information provider according to claim 10, wherein the pre-prepared data may be read by said reader when said information provider is in the vicinity of said reader.

12. An information provider according to claim 1, wherein the information provider is designed and intended to be entered into said medical waste container.

13. An information provider according to claim 1, wherein said data carrier comprises optically readable elements.

14. An information provider according to claim 1, wherein said data carrier comprises near frequency communication elements.

15. An information provider according to claim 1, wherein said body is made of material of sheet form.

16. An information provider according to claim 15, wherein the sheet material comprising thin sheets of plastic, metal, wood, cardboard, paper or laminated combinations thereof.

17. An information provider according to claim 1, wherein the information provider is comprised in a primary package for a medicament.

18. The information provider according to claim 1, wherein the reader is operably connected to a medical waste container.

19. The information provider according to claim 18, wherein the reader is positioned in a base on which said medical waste container may be placed.

20. An information provider for providing information on perceived health status of a patient, comprising
    a body having an outer surface, where the body contains handling instructions that informs a user of the information provider how to use the information provider to communicate a specific health status of the user;
    a data carrier, where at least a portion of the data carrier is located on the outer surface, where the data carrier contains pre-prepared data comprising a number of possible health statuses of a user of the information provider; and a material covering the data carrier such that the pre-prepared data is not accessible to the user, wherein the user must physically remove the material from the data carrier so that the pre-prepared data becomes accessible to allow the user to select from the pre- prepared data the specific health status that is indicative of the health status of the user at the time the selection is made by the user, wherein after the selection of the specific health status, the data carrier will then provide the specific health status to a reader configured to read the data carrier.

\* \* \* \* \*